United States Patent [19]

Smith et al.

[11] Plant 4,683

[45] Apr. 7, 1981

[54] ALMOND TREE

[76] Inventors: Earl Smith, 2764 N. Leonard; Alba E. Wimer, 2826 N. Leonard, both of Fresno, Calif. 93727

[21] Appl. No.: 103,545

[22] Filed: Dec. 14, 1979

[51] Int. Cl.[3] ..... A01H 5/03

[52] U.S. Cl. ..... Plt./30

[58] Field of Search ..... Plt./30

*Primary Examiner*—Robert E. Bagwill

*Attorney, Agent, or Firm*—Victor Sepulveda

[57] ABSTRACT

Herein described is an almond tree which exhibits heavy clusters of almonds on a tree having sturdy branches and producing a sweet tasting nut of excellent quality with a semi-soft shell and characterized by the fact that it blooms at about the same time as the Nonpareil (unpatented) and is harvested immediately after the Nonpareil.

2 Drawing Figures

ORIGIN OF THE VARIETY

We first discovered a new and distinct open pollinated seedling in a cultivated state on our ranch in Fresno County, Calif. The ranch in which the seedling was first discovered includes an orchard of the Nonpareil variety and the Texas Mission variety with the rows thereof interposed with one another for open pollination of the varieties. The seedling almond tree which resulted from the above-described crops was maintained by us under careful and continued observation and we recognized its new and distinct characteristics which classed it as a commercially desirable variety. The variety was therefore selected for asexual reproduction in preparation to ultimate commercial planting thereof.

ASEXUAL REPRODUCTION OF THE VARIETY

Upon recognition by us of the novel and distinct characteristics (as hereinafter described) of the original tree for the present variety we selected for further testing and observation which included asexual reproduction of the variety accomplished under my control and direction by budding onto a mature Nemaguard peach root stock. We ascertained that such asexual reproduction ran true to the original tree in all respects and that such variety had substantial commercial potential.

SUMMARY OF THE VARIETY

We particularly noticed that the nut from the tree had a semi-soft shell when compared to the Nonpareil which has a soft shell. This characteristic has a basic advantage of warding off insects and keeps the edible part thereof intact. The nut itself was found to be sweeter in taste than the Nonpareil.

Further, the almonds on the tree tend to cluster more on the branches than do the Nonpareil which then provides a greater yield at harvest. Adding to this is the feature of the branches being somewhat stronger and allowing them to support the higher yield of nuts.

We also found that a basic novel feature of the new and distinct variety of almond tree is the fact that it blooms much the same time as the Nonpareil with full blooms and longer pistils. Because of the fact that this new variety blooms at the same time as the Nonpareil, it makes it ideal for use as a cross-pollinator for the Nonpareil.

BRIEF DESCRIPTION OF THE DRAWING

The drawing is an illustration by photographic reproduction in color of a cluster of almonds, a detached almond showing in its shell, and a second almond which is removed from its shell.

DESCRIPTION OF THE VARIETY

The botanical details of this new distinct variety of almond tree with color definitions (except those in commercial terms) referenced by Maerz and Paul Dictionary of Color are as follows:

Tree: Mostly medium in size; medium vigor; spreading; round top; medium foliage; hardy; heavy regular production.

*Distribution of nuts on tree.*—Many in clusters, well and evenly distributed.

Trunk: Medium size.

*Bark.*—Medium.

*Texture.*—Medium.

Branches: Internodes, medium.

*Length of new growth.*—Mostly medium.

*Branching habit.*—Medium.

*Spurs.*—Many with clusters of fruit buds.

*Branching angle.*—Wide angle on older branches.

*Lenticels.*—Numerous; small on fine wood; vary from none to numerous, depending upon age of wood.

*Color.*—New wood—glossy, darker green with slight brown overcast on dorsal side; dull, light green on ventral side. Mature wood—mostly gray; glossy brown with the over bark gray, older wood mostly gray on dorsal side; dull, light green with overcast on ventral side.

Leaves: Mostly medium to small (about 84 mm long, 26 mm wide); abundant; lanceolate.

*Leaf apex.*—Acutely pointed.

*Leaf thickness.*—Thin.

*Texture.*—Smooth.

*Color.*—Grassy medium green (M & P 23-J-7), dorsal side; dull medium green (M & P 22-E-8) ventral side.

*Leaf base.*—Broadly acute to mostly obtuse.

*Leaf vein.*—Pinnately net veined.

*Midrib.*—Pronounced to heavy.

*Margin.*—Glandular; crenate.

*Leaf conformation.*—Flat.

*Petiole.*—Medium length (about 24 mm); slender thickness (about $\frac{7}{8}$ mm). Color—Absinthe Green (M & P 20-I-6) on dorsal side; Reed Green (M & P 19-F-2) on ventral side.

*Glands.*—Number—about 3.7, vary from about 2 to about 5. Position—mixed, mostly opposite, some alternate. Size—small. Form—mixed, mostly globose, few reniform. Color—mixed, few red, mostly green. Position on leaf—mostly on petiole. Stipules—very few to many on current season's growth.

*Leaf buds.*—Small; pointed; many renewal leaf buds on spurs.

Flowers:

*Flower buds.*—Heavy; date of first bloom—about February 20. Date of full bloom—about March 9.

*Period of bloom.*—Midseason; first bloom and full bloom about 2 to 3 days after Nonpareil; about 10 to 12 days ahead of Texas Mission and Carmel.

*Size of blossoms.*—Mostly large.

*Color of bloom.*—Pinkish white.

*Pistils.*—Number, 1.

*Stamens.*—Number about 27 to 35, average 29.

*Anthers.*—Large.

Crop:

*Tenacity.*—Hangs on tree mostly tightly.

*Hulling.*—Easy to hull.

Hull:

*Outer surface.*—Medium smooth; light pubescence.

*Pits.*—None.

*Thickness.*—Medium to thin.

*Flesh.*—Slightly fleshy, tough to medium.

*Color.*—Mostly light greenish yellow with some silvery sheen with grayish overcast (M & P 20-H-3), spotted with gray color, blushed with light green.

*Dehiscence.*—Opening freely, started about July 15.

*Splitting.*—Along ventral suture, freely at base.

Nut:

*Size.*—Medium; length about 29+ mm; width, about 20.8 mm; thickness, about 14.6 mm; weight (30 in shell) = about 2 ounces each = about 0.0666 ounces.

*Form.*—Width/length × 100 = about 72 rating, ovate; width/thickness about 20.8/14.6 = about 1.42 mm, plump.

*Shell.*—Paper: medium soft, medium thin, medium smooth. Outer shell—medium hard. Inner shell—medium soft, well sealed. Color—medium light to dark, (M & P 10-E-3). Pits—large, numerous, deep to mostly medium shallow; round to irregular. Base—mostly square to slightly dorsally oblique. Stem scar—medium, obtuse. Apex—obtuse, sharp, broadly curved on dorsal-ventral side. Wing—mostly broad, some medium, thin, mostly full from base to apex. Inner surface—medium to light, lightly streaked. Ventral streak—dark, broad, long, point obtuse, corky. Percent kernel to nut: 50 percent; 30 in shell = about 2 ounces, 30 kernels = about 1 ounce.

Kernel:

*Size.*—Mostly medium to small, length about 18.8 mm; width about 13 mm; thickness about 8 mm; weight about 0.0333 ounces each.

*Form.*—Width/length = about 0.69; ovate, slightly elongated; width broad at base end = about 13/8 = about 1.625 mm.

*Plumpness.*—Medium, many flat.

*Base.*—Mostly square, ventrally oblique.

*Stem scar.*—Medium; obtuse; mostly light brown.

*Apex.*—Obtuse, sharp point; tip recurved slightly toward dorsal edge.

*Smoothness.*—Wrinkled, furrowed.

*Pellicle.*—Medium to thin; very few folds.

*Pubescence.*—Medium.

*Color.*—Light brown to brown (M & P 13-E-9).

*No. doubles.*—None.

*Defective kernels.*—Gummy: very few to none. Corky: none. Blanks: none. Deformed: very few. Shriveled: very few.

*Flavor.*—Sweet, above normal in sweetness, taste very pleasing, no bitterness.

*Quality.*—Very good.

*Susceptibility or resistance to insects.*—Good. Normal resistance to almond mites, controlled by spray program, need control and early harvest.

*Susceptibility to disease.*—Good, normal resistance to Split Hale Fungus and Brown Rot, controlled with proper sprays.

Although the new variety of almond tree possesses the described characteristics of the growing traditions in Fresno County, Calif. in the central portion of the San Joaquin Valley where the new variety was first observed, it is understood that variations of the usual magnitude and characteristics instant to environment and treatment are to be expected.

Having thus described and illustrated my new variety of almond tree, what is claimed as new and desired to be secured by Letters Patent is:

1. A new and distinct variety of almond tree substantially as shown and described.

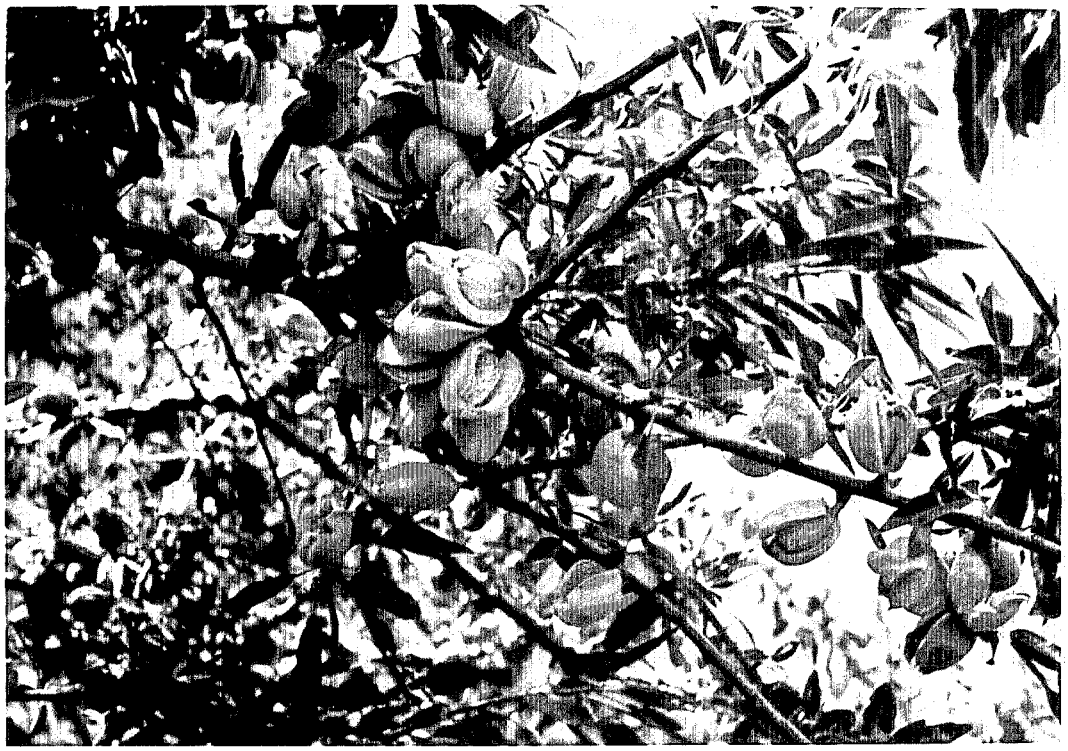
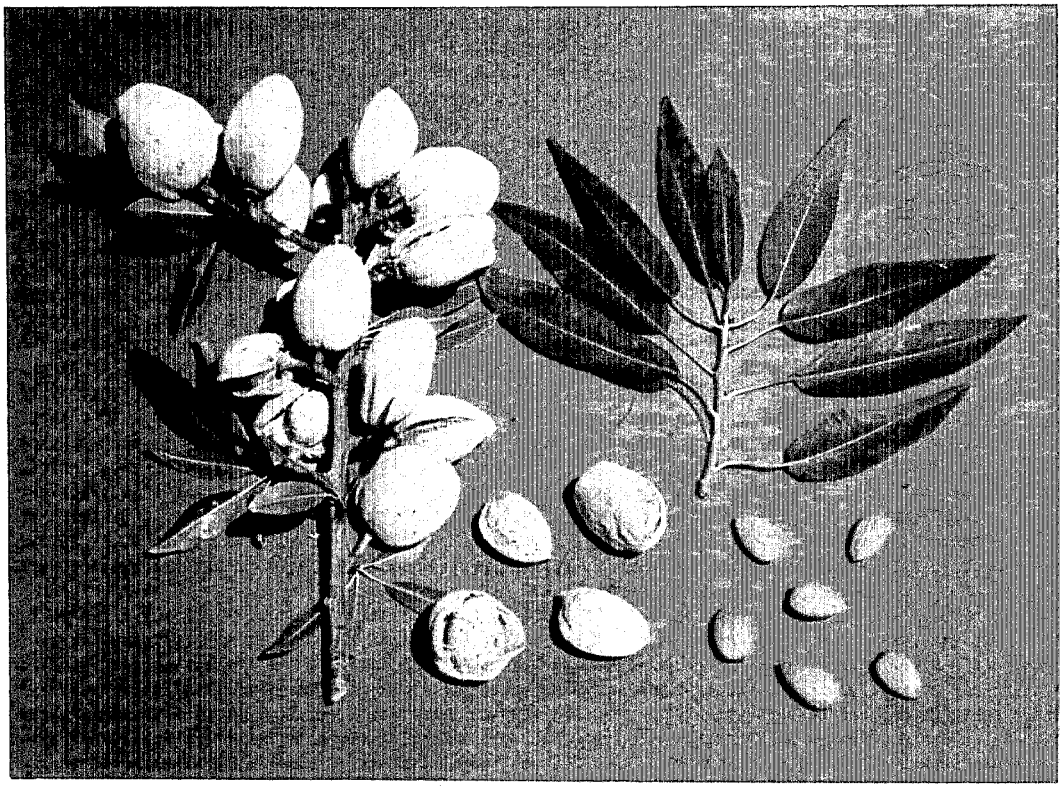

* * * * *